United States Patent [19]

Decker et al.

[11] Patent Number: 5,618,436

[45] Date of Patent: Apr. 8, 1997

[54] PROCESS FOR CLARIFYING METAL ALKYLS

[75] Inventors: L. Ben Decker, Lago Vista; Mark W. Hellums, Austin, both of Tex.; Mark M. Chavez, Lake Charles, La.

[73] Assignee: CONDEA Vista Company, Houston, Tex.

[21] Appl. No.: 602,983

[22] Filed: Feb. 16, 1996

[51] Int. Cl.$^6$ .................................................. B01D 61/00
[52] U.S. Cl. ........................... 210/651; 210/641; 210/650; 210/636; 210/805
[58] Field of Search .................................... 210/651, 641, 210/653, 654, 650, 652, 636, 805, 195.2, 500.27, 644; 585/823, 829, 830

[56] References Cited

U.S. PATENT DOCUMENTS

| | | |
|---|---|---|
| 2,863,894 | 12/1958 | Smith . |
| 2,900,402 | 8/1959 | Johnson . |
| 2,931,820 | 4/1960 | Barclay et al. . |
| 2,987,534 | 6/1961 | Shapiro et al. . |
| 3,020,574 | 2/1962 | Vosbikian et al. . |
| 3,030,401 | 4/1962 | Movsovic et al. . |
| 3,050,540 | 8/1962 | Gould . |
| 3,076,006 | 1/1963 | Kinter et al. . |
| 3,149,179 | 9/1994 | Bowden ................................. 210/644 |
| 3,207,770 | 9/1965 | Ziegler et al. . |
| 3,207,772 | 9/1965 | Ziegler et al. . |
| 3,207,773 | 9/1965 | Ziegler et al. . |
| 3,207,774 | 9/1965 | Ziegler et al. . |
| 3,617,553 | 2/1971 | Westaway .............................. 210/651 |
| 3,645,891 | 2/1972 | Goldup et al. ........................ 210/653 |
| 4,251,453 | 2/1981 | Garrison . |
| 4,952,317 | 8/1990 | Culkin .................................. 210/636 |
| 5,151,182 | 9/1992 | Perry et al. ........................ 210/500.27 |
| 5,174,899 | 12/1992 | Bahrmann et al. .................... 210/651 |
| 5,245,105 | 9/1993 | Lin et al. . |
| 5,276,244 | 1/1994 | Lin et al. .............................. 210/651 |

OTHER PUBLICATIONS

*V–SEP Series i User Manual*, Version 3.0, New Logic International, Nov. 1994.

Schweitzer, A. Philip, "Handbook of Separation Techniques for Chemical Egineers", pp. 2–33., McGraw Hill Book Company.

Primary Examiner—Ana Fortuna
Attorney, Agent, or Firm—Browning Bushman

[57] ABSTRACT

A process for clarifying a metal alkyl reaction product comprising passing a first feed stream comprising metal alkyls, a first, substantially water-immiscible organic solvent, and solid contaminants through a first membrane filter, the first filter being substantially continuously vibrated when said feed stream is passing through and recovering from the first filter a first permeate substantially free of solid contaminants and a first concentrate containing solid contaminants.

13 Claims, 1 Drawing Sheet

PROCESS FOR CLARIFYING METAL ALKYLS

BACKGROUND OF THE INVENTION

1. Field of the Invention

The present invention relates to the purification of crude metal alkyls containing solid particulate contaminants and, more particularly, to the clarification of aluminum alkyls containing such contaminants.

2. Description of the Prior Art

Fatty alcohols find widespread industrial use as, for example, in the manufacture of surfactants. While these alcohols can be derived from natural sources such as animal fats and vegetable oils, they can also be produced synthetically via Ziegler chemistry. In the Ziegler process, an olefin (usually ethylene) is polymerized onto a trialkyl aluminum such as triethyl aluminum in what is known as a "growth reaction" to produce higher straight chain aluminum alkyls. These alkyls are then oxidized to produce the corresponding alkoxide, which, upon hydrolysis, forms the corresponding alcohol.

Most commercial alcohol processes utilizing Ziegler chemistry utilize a growth reaction, e.g., adding ethylene to aluminum diethyl hydride to manufacture normal primary alcohols with an even number of carbon atoms in each chain. The nature of the materials handled throughout the process creates many problems. For example, in the case of aluminum alkyls, dense slurries of aluminum and aluminum triethyl (ATE) and solvent must be handled in pipelines and pumped at high pressures. ATE is pyrophoric and decomposes explosively in the presence of water and, accordingly, can be very dangerous if not handled properly. Although ATE can be diluted with inert solvent, making handling somewhat less dangerous, care must still be taken to prevent spills or leaks in any plant stream that contains ATE.

Typically, crude aluminum alkyls, e.g., ATEs, are produced from aluminum powder, hydrogen, and ethylene. The crude product consists of aluminum alkyls, most of which are aluminum triethyl, a solvent diluent such as kerosene or another inert hydrocarbon, and a finite amount of solid contaminants such as fine aluminum powder. These solid contaminants must be removed in order to obtain a product suitable for subsequent uses such as in a growth reaction wherein higher carbon chain aluminum alkyls are produced. The presence of these solid contaminants in the crude aluminum trialkyl (ATA) stream causes it to have a very dark or black appearance. Generally speaking, solid impurities including the aluminum fines are present in the crude ATA in an amount of up to about 15% by weight.

Numerous techniques have been employed in an attempt to commercially remove solid impurities from ATA streams. U.S. Pat. No. 2,863,894 teaches the filtration of aluminum alkyls. U.S. Pat. No. 2,900,402 shows that aluminum diethyl hydride present after a hydrogenation reaction can be filtered or decantered to remove aluminum fines. U.S. Pat. No. 2,931,820 teaches purification of an aluminum alkyl by filtration. U.S. Pat. No. 2,987,534 teaches the removal of suspended aluminum by centrifuging. U.S. Pat. No. 3,030,401 teaches the removal of aluminum powder by filtering the reaction solution in the presence of a filter aid such as bentonite clays. U.S. Pat. No. 3,032,574 teaches the removal of suspended aluminum impurities by centrifuging, vacuum distillation, or filtration. U.S. Pat. No. 3,050,540 teaches the removal of excess aluminum from aluminum alkyls by filtration. U.S. Pat. No. 3,076,006 teaches that suspended solids can be removed by filtration. U.S. Pat. Nos. 3,207,770; 3,207,772; 3,207,773; and 3,207,774 all disclose that suspended aluminum in aluminum trialkyl products can be removed by distillation, centrifuging, or filtration.

None of the filtration methods described heretofore have proven to be commercially viable for removing the solid impurities, including the aluminum fines, from ATA streams. Indeed, the use of prior art filtration methods have proven to be highly dangerous and unreliable due to constant plugging of the filters, the need for replacement, and cracking under high pressures, resulting in aluminum alkyl spills, which, as noted above, can be extremely hazardous, both to personnel and equipment because of the pyrophoric nature of the aluminum alkyls. Accordingly, the use of filters as a means of removing solid impurities from ATA streams has been largely discontinued in commercial operations and replaced by vacuum distillation.

While vacuum distillation can successfully remove the solid impurities from the ATA streams, such processes are inefficient both in energy consumption and lost product in that some of the ATAs, e.g., aluminum trioctyl, will decompose at the temperature needed to conduct the distillation. It is clear that filtration, if it could be conducted safely, continuously, and over long run times, would be the preferred method of purifying ATA streams.

SUMMARY OF THE INVENTION

It is therefore an object of the present invention to provide an improved process for separating solid contaminants such as metallic fines from metal alkyl streams.

Another object of the present invention is to provide a filtration method for removing solid contaminants from metal alkyl streams in a safe and continuous manner.

A particular object of the present invention is to provide a process for clarifying metal alkyl streams such as aluminum trialkyls.

The above and other objects of the present invention will become apparent from the drawings, the description give herein, and appended claims.

According to the present invention, a metal alkyl reaction product is clarified by passing a feed stream comprising a metal alkyl, a water-immiscible organic solvent, and solid contaminants through a first vibrating membrane filter, the filter being substantially continuously vibrated as the first stream is passed therethrough, there being recovered from the first filter a permeate substantially free of solid contaminants and a concentrate containing solid contaminants.

DESCRIPTION OF THE PREFERRED EMBODIMENTS

Figure 1:
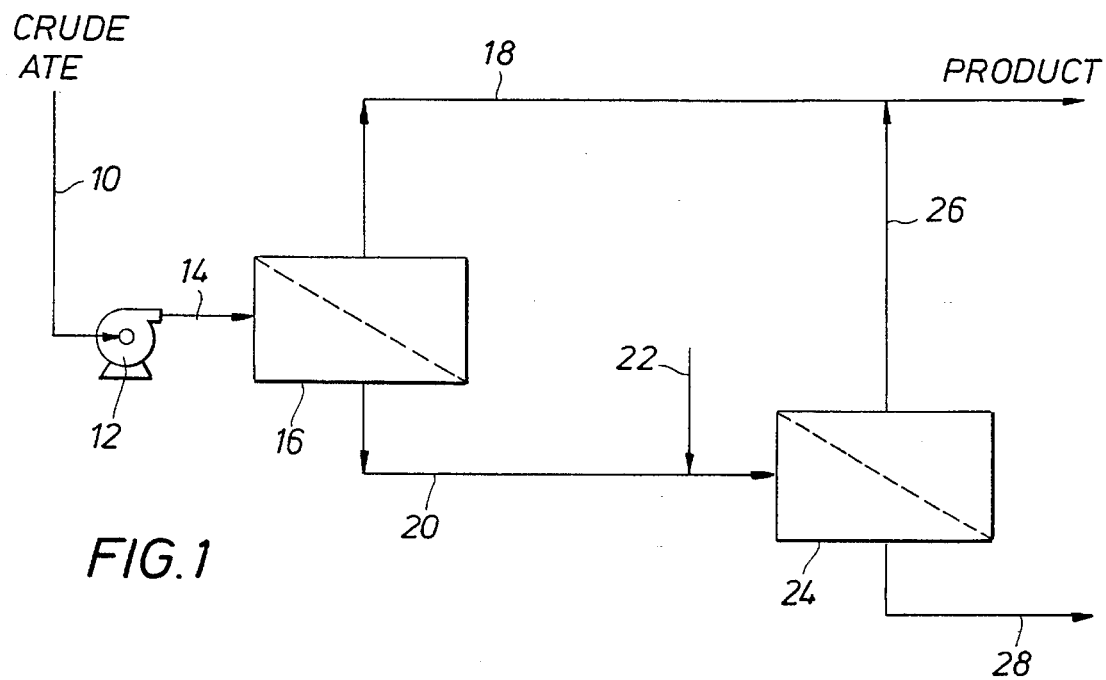
FIG. 1 is a simplified schematic drawing of one embodiment of the process of the present invention configured in a continuous mode using two stages of filtration.

The metal alkyls that can be purified according to the process of the present invention can comprise any metal alkyl that is liquid or soluble in a suitable solvent. Thus, alkyls of such metals as vanadium, titanium, and the like can be purified according to the process of the present invention.

Accordingly, while the present invention will be described with particular reference to the purification of aluminum alkyls, it will be understood that it is not so limited.

The aluminum alkyls that can be purified according to the process of the present invention can comprise any aluminum trialkyl that is liquid or soluble in a suitable solvent. Typically, such ATAs are made, as discussed above, by reacting aluminum powder, hydrogen, and an alkene containing from 2 to 18 carbon atoms such as ethylene, propylene, hexene, octene, or the like. The crude product consists of aluminum alkyls that, when ethylene is used, are primarily aluminum triethyls, a solvent/diluent such as kerosene or some other inert liquid hydrocarbon, and solid contaminants such as residual aluminum fines. Typically, the ATA reaction product mixture that can be purified or clarified according to the process of the present invention will contain at least 70% by weight ATA, preferably at least 80% by weight ATA, the amount of solid contaminants being present in an amount of less than about 15% by weight, generally less than about 10% by weight, most preferably less than about 5% by weight.

The vibrating membrane filters that can be used in accordance with the process of the present invention are described and claimed in U.S. Pat. No. 4,952,317, incorporated herein by reference for all purposes. Briefly, the vibrating membrane filters comprise a permeable membrane mounted on a support, the permeable membrane having an exterior surface and forming an interior chamber. The filter includes an outlet for permeate passing through the membrane into the interior chamber. The filter is disposed in a suitable vessel containing the suspension to be filtered, the filter being connected to a means for vibrating the filter tangentially along the exterior surface of the membrane whereby shearing is induced between the exterior surface of the membrane and the suspension to be filtered. Negative or positive pressure can be used to motivate permeation of selected components of the suspension through the membrane for collection.

A commercially available vibrating membrane filter system is available from New Logic International under the trade name V-SEP (Vibratory Shear Enhanced Processing). In the V-SEP system, the filter elements described above are arrayed as parallel disks separated by gaskets, baffels, and diverters. This disk stack is spun in a torsional oscillation to produce the desired shear rate at the membranes. Vibrating membrane filters such as the V-SEP unit are typically operated at pressures (transmembrane pressure) of from about 50–175 psi, which is the pressure of the suspension acting against the membrane and created by a suitable source such as a feed pump. In the V-SEP system, as the feed cascades from disk to disk, solids are concentrated, allowing substantially solid-free permeate to be collected interiorally of the membranes and a concentrated feed slurry to be recovered externally of the membranes.

Generally speaking, the transmembrane pressure employed in the process of the present invention, i.e., the pressure acting on the crude feed, will be positive super atmospheric pressure applied by a pump and from about 40 to about 150 psig, more generally from about 60 to about 80 psig, temperatures ranging from 40–150° F. The membrane flux, defined as gal/ft$^2$/day (GFD), will vary considerably depending upon amplitude, concentration of solids in the feed, operating pressures and temperatures, and other such parameters well known to those skilled in the art. Generally, the flux will range from 10 to 100 GFD. Generally speaking, the membranes will be vibrated at a frequency of between about 20 Hz (cycles/sec) and 150 Hz, frequencies of from about 20–75 Hz being preferred. The displacement amplitude of the vibrations on the filters can be varied over wide limits generally ranging from about 0.2 to about 1 inch. It has generally been found that shear intensities ranging from about 50 to about 400,000 sec$^{-1}$ or more can be employed.

In conducting the process of the present invention, it has been found necessary to continuously shear the feed; i.e., the filter is vibrated substantially continuously at the desired frequency and amplitude during filtration. It has also been found that steady-state membrane flux can be temporarily boosted by periodically interrupting flow to the filters while continuing the membrane vibration. This procedure, referred to as a "shake test," serves to reduce the thickness of the solid layer that attaches to the membrane surface. In conducting this shake test, the flow of feed to the filters will normally be interrupted for a period of from 1 to 3 minutes, depending upon how long the filters have been operating, the concentration of solids in the feed, and other parameters that contribute to buildup of solid cake on the membranes. Indeed, it has surprisingly been found that this shake test is more effective at sustaining high flux than either increasing or decreasing transmembrane pressure.

It will be recognized that the degree of clarification or removal of solids from the aluminum alkyl feed is a function of the pore size of the membrane. Generally speaking, the membrane filters of the present invention will have a pore size of about 2μ or less, preferably a pore size of about 1μ or less. Using filters with such pore sizes, one can achieve a permeate containing solids in an amount insufficient to exhibit a Tyndall Effect—i.e., a highly clarified permeate is obtained.

Figure 2:
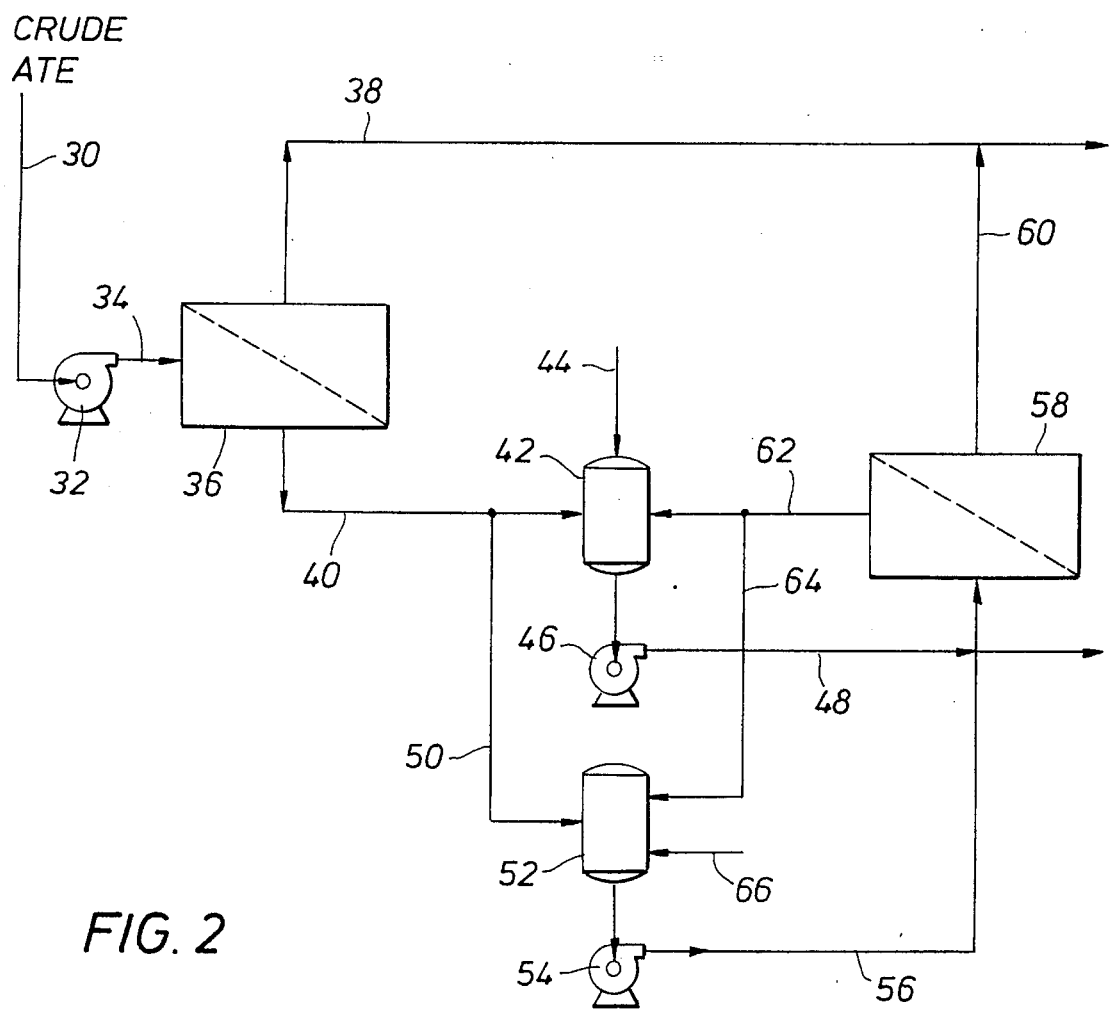
FIG. 2 is a simplified schematic drawings of another embodiment of the process of the present invention configured such that the second stage of filtration is operated in a semi-batch mode.

To further illustrate the present invention, reference is made to FIGS. 1 and 2 showing continuous and semi-batch methods, respectively, for conducting the process of the present invention. With reference first to FIG. 1, crude ATE containing about 85% by weight ATE and about 1% by weight particulate aluminum and other solids is fed via line 10 by a pump 12 through line 14 into first vibrating membrane filter 16. A substantially solid-free permeate is removed from vibrating filter 16 via line 18 and recovered as a product for further use in a growth reaction. A concentrate containing solids is removed from vibrating filter 16 via line 20, combined with further solvent via line 22, and introduced into second vibrating filter 24. Solids-free permeate is removed from vibrating filter 24 via line 26 to be combined with permeate in line 18 while a concentrate containing solids is removed from filter 24 via line 28. In the configuration shown in FIG. 1, the system can be operated continuously; i.e., clarified permeate and concentrated solids (concentrate) are continuously removed via lines 18 and 28, respectively.

With reference now to FIG. 2, the process of the present invention will be described on the basis of semi-batch operation. Crude ATE is introduced via line 30, pump 32, and line 34 into first vibrating membrane filter 36. Solids-free permeate is removed from filter 36 via line 38 for recovery as product to be sent to a growth reaction process. A solids-containing concentrate is removed from filter 36 via line 40 and transferred to either of recovery tanks 42 or 52, into which is introduced additional solvent via lines 44 or 46, respectively, at required intervals to maintain the solids concentration at a preselected value. When the concentrate from filter 36 is being transferred to transfer tank 42, concentrate from tank 52 is removed via pump 54 and line 56 and introduced into second vibrating filter 58. A solids-free permeate is removed from second vibrating filter 58 via line 60 and combined with permeate in line 38 to be recovered as product. Concentrate from second filter 58 is removed via line 62 and line 64 and transferred into recovery tank 52. When the desired ATA concentration is reached in recovery tank 52, the enriched concentrate (low ATA concentration) stream is purged from the system via lines 56 and 61. When the concentrate from filter 36 is transferred to tank 52, concentrate from tank 42 is removed via pump 46 and line 48 and introduced into the second filter 58. Concentrate from second filter 58 is removed via line 62 and transferred into recovery tank 42. When the desired ATA concentration is reached in recovery tank 52, the enriched concentrate (low ATA concentration) stream is purged from the system via lines 48 and 61. In the operation depicted in FIG. 2, the process is semi-batch in the sense that concentrate removed from recovery tank 42 is intermittently pumped off. Thus, the process depicted in FIG. 2 is semi-batch only in the sense that concentrate is intermittently removed from the system, whereas permeate is continuously removed from the system.

To more fully illustrate the present invention, the following non-limiting example is presented.

EXAMPLE

In an actual plant test, a New Logic International, New Logic I vibrating membrane filter system was employed. The membrane was of Teflon, having a pore size of $0.2\mu$ supported on fiberglass. The transmembrane pressure was 60 psig, and the temperature, 120° F. The membrane flux was 35 GFD. The membrane was vibrated at an amplitude of ¾ inch and a frequency of 55 Hz (steady state operation). The feed consisted primarily of aluminum triethyl with 5% by weight aluminum diethyl hydride, 5% aluminum tributyl, 7.2% by weight kerosene (solvent), and 0.8% by weight aluminum metal and other solids. The permeate was found to be essentially free of solids; i.e., the solids present were insufficient to exhibit a Tyndall Effect.

What is claimed is:

1. A process for clarifying a metal alkyl reaction product, comprising:

passing a first feed stream comprising a metal alkyl, a first, substantially water-immiscible organic solvent, and solid contaminants through a first vibrating membrane filter, said first filter being substantially continuously vibrated while said first feed stream is passing therethrough;

periodically interrupting the flow of said first feed stream through said first vibrating membrane filter while continuing to vibrate said first vibrating membrane filter; and recovering from said first filter a first permeate substantially free of said solid contaminants and a first concentrate containing said solid contaminants.

2. The process of claim 1 wherein said first permeate contains solids in an amount insufficient to exhibit a Tyndall Effect.

3. The process of claim 1 comprising admixing said first concentrate with a second, substantially water-immiscible organic solvent to produce a second feed stream, passing said second feed stream through a second vibrating membrane filter, recovering a second permeate substantially free of said solid contaminants and a second concentrate containing said solid contaminants, said second filter being substantially continuously vibrated while said second feed stream is passing therethrough.

4. The process of claim 3 conducted on a continuous basis.

5. The process of claim 3 comprising recovering said second concentrate on a batch basis.

6. The process of claim 3 wherein said first and second feed streams are subjected to super atmospheric pressure.

7. The process of claim 6 wherein said pressure is from about 40 to about 150 psi.

8. The process of claim 3 wherein the temperature of said first and said second feed streams is from about 40° F. to about 150° F.

9. The process of claim 3 wherein said first and second filters have a pore size of about $2\mu$ or less.

10. The process of claim 9 wherein said first and second filters have a pore size of less than about $1\mu$.

11. The process of claim 3 wherein said flow of said second feed stream to said second filter is interrupted intermittently, said filter being vibrated during such interrupted flow.

12. The process of claim 1 wherein said solid contaminants in said first stream are present in an amount of less than about 15% by weight.

13. The process of claim 1 wherein said first feed stream comprises an aluminum trialkyl in an amount of at least about 70% by weight.

* * * * *